United States Patent [19] [11] Patent Number: 5,384,033
Matasovic [45] Date of Patent: Jan. 24, 1995

[54] FLOATING INLET TUBE

[75] Inventor: Jozef D. Matasovic, Salt Lake City, Utah

[73] Assignee: Baker Hughes Incorporated, Houston, Tex.

[21] Appl. No.: 207,753

[22] Filed: Mar. 8, 1994

[51] Int. Cl.⁶ ............................................. C02F 3/28
[52] U.S. Cl. ............................... 210/121; 210/242.1; 210/DIG. 9; 366/279
[58] Field of Search ............ 210/121, 122, 219, 242.1, 210/242.3, 603, DIG. 9; 366/279, 318

[56] References Cited

U.S. PATENT DOCUMENTS

| | | | |
|---|---|---|---|
| 1,912,595 | 6/1933 | Schlenz | 210/DIG. 9 |
| 3,187,897 | 6/1965 | Walker | 210/DIG. 9 |
| 3,288,295 | 11/1966 | Kelly | 210/121 |
| 3,303,932 | 2/1967 | Hirs et al. | 210/242.3 |
| 3,535,236 | 10/1970 | Travis | 210/DIG. 9 |
| 3,633,749 | 1/1972 | Panosh | 210/242.1 |
| 4,024,062 | 5/1977 | Holthuis | 210/219 |
| 4,094,338 | 6/1978 | Bauer | 210/242.1 |
| 4,153,071 | 5/1979 | Black et al. | 137/386 |
| 4,378,437 | 3/1983 | Cook | 210/DIG. 9 |
| 4,391,705 | 7/1983 | Cook et al. | 210/218 |
| 4,422,771 | 12/1983 | Earhart | 366/251 |
| 4,540,528 | 9/1985 | Haegeman | 366/279 |
| 4,575,256 | 3/1986 | Armitage et al. | 366/266 |
| 4,626,358 | 12/1986 | Fetsko | 210/242.3 |
| 4,663,037 | 5/1987 | Breslin | 210/242.1 |
| 4,695,376 | 9/1987 | Astrom et al. | 210/242.1 |
| 4,761,225 | 8/1988 | Breslin | 210/242.3 |
| 4,956,100 | 9/1990 | Mikkleson | 210/242.3 |
| 4,997,557 | 3/1991 | Andersen | 210/242.2 |
| 4,998,585 | 3/1991 | Newcomer et al. | 210/242.3 |
| 5,104,528 | 4/1992 | Christie | 210/242.1 |

Primary Examiner—Christopher Upton
Attorney, Agent, or Firm—Trask, Britt & Rossa

[57] ABSTRACT

A floating inlet assembly for use with a mixing apparatus in a digester. The floating inlet assembly comprising a floating inlet housing which is vertically reciprocable with respect either to a fixed inlet tube or to a guide tube structure.

22 Claims, 6 Drawing Sheets

FLOATING INLET TUBE

BACKGROUND OF THE INVENTION

1. Field of the Invention

The invention relates to an improved mixing device for use in biological reactor apparatus. More specifically, this invention relates to an improved float tube assembly for a sludge mixing apparatus for use in digesting apparatus for treating municipal waste sludge and the like.

Typically, digesting apparatus for treating municipal sludge waste comprises a tank having an inlet and outlet and a floating or fixed cover or dome. Gas evolving material, commonly referred to as sludge, to be anaerobically digested is admitted through the sludge feed pipe (inlet) to the digester, while supernant or treated material is withdrawn through the outlet located at the desired surface level of the liquid.

2. State of the Art

During the anaerobic digestion of the sludge gas evolves and is trapped under the cover of the digester. Since the rate of gas production varies it is desirable to use floating ballast type covers for the digester. Such covers are shown in U.S. Pat. Nos. 3,535,236, 4,378,437 and 4,391,705.

To enhance the rate of the digestion of the organic material in the sludge, it is desirable to mix the contents of the digester. Typical prior art mixing apparatus for use in digesters are shown in U.S. Pat. Nos. 4,422,771, 4,575,256 and 4,997,557. To promote efficient mixing of the sludge in the digester it is preferred that the liquid, scum, and any foam thereon be continuously mixed into the materials in the lower part of the digester. Since the fluid level in the digester can vary as well as the amount of free liquid, scum and any foam thereon, even though the digester may include a floating cover, accurate vertical placement of the mixing apparatus within the digester is difficult to ensure that at any point in time the mixing apparatus inlet will have access to free liquid, scum and any foam thereon for mixing into the material therebelow. If the mixing apparatus does not have access to liquid to mix into the sludge, little beneficial mixing of the sludge can take place. It is also desirable that the mixing apparatus have access to any scum and foam on the surface of the liquid in the digester so that the mixing apparatus can break down the scum and foam.

Various types of floating inlet and skimming apparatus for digesters are illustrated in U.S. Pat. Nos. 3,303,932, 4,094,338, 4,153,071, 4,024,062 and 4,956,100. Other types of skimming apparatus are illustrated in U.S. Pat. Nos. 3,633,749, 4,663,037, 4,761,225, 4,626,358 and 4,998,585.

BRIEF SUMMARY OF THE INVENTION

The present invention is directed to a floating inlet assembly for a mixing apparatus for use in a digester or biological reactor apparatus. The present invention of a floating inlet assembly may comprise several arrangements depending upon the location of the mixing apparatus with respect to the digester or biological reactor apparatus. The floating inlet assembly for a mixing apparatus comprises a floating inlet housing which is vertically reciprocable with respect either to a fixed inlet tube or to a guide tube structure.

The present invention will be better understood when the drawings are taken in conjunction with the detailed description of the invention hereafter.

DETAILED DESCRIPTION OF THE INVENTION

Figure 1:
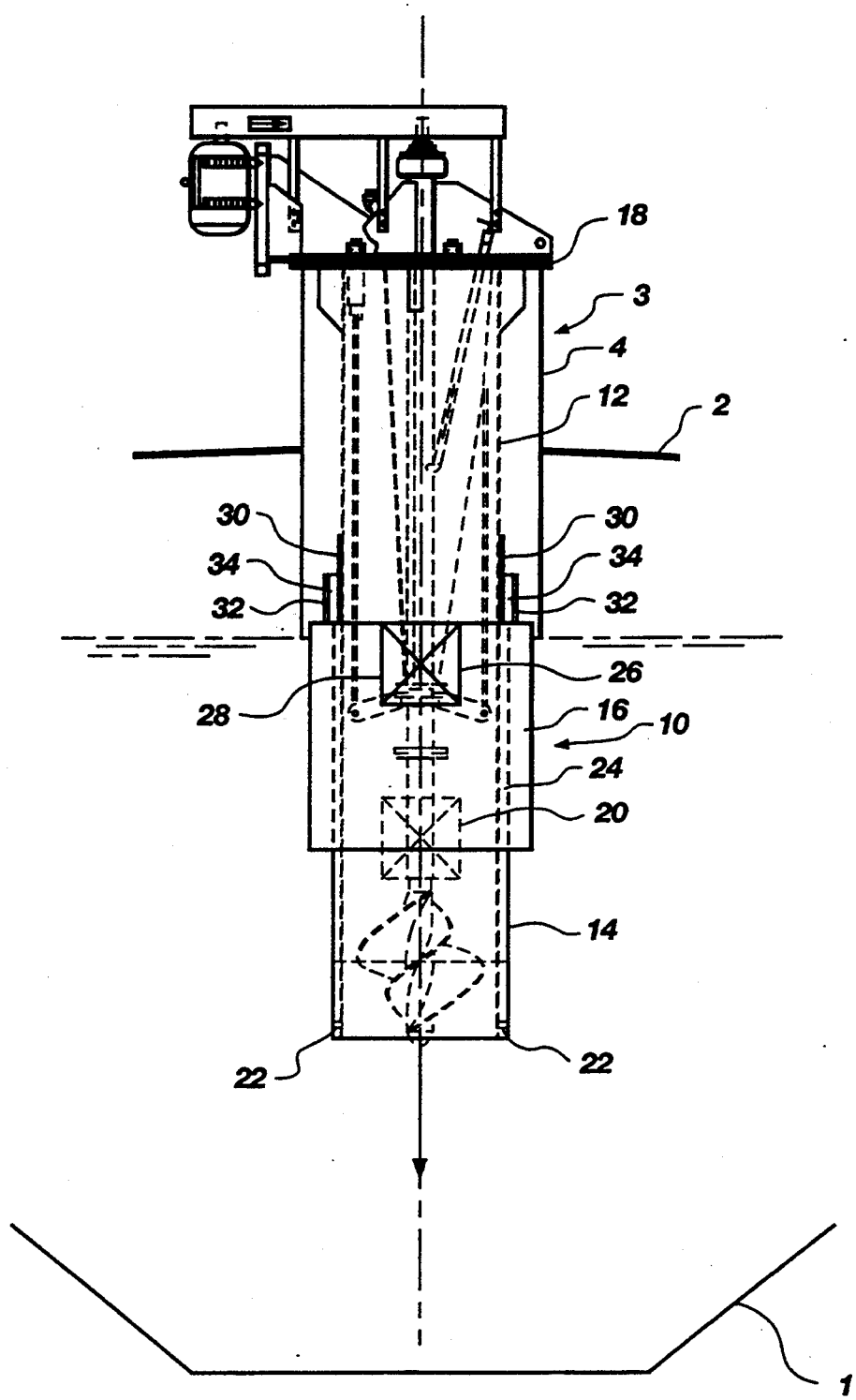
FIG. 1 is a side view of an embodiment of the present invention in a digester at its upper liquid level.

Referring to drawing FIG. 1, a first embodiment 10 of the float tube assembly of the present invention is shown.

The float tube assembly 10 of the present invention is shown in a digester 1 having a floating cover 2 and mixing apparatus 3 installed therethrough. The mixing apparatus 3 may be of any suitable configuration such as illustrated in U.S. Pat. No. 4,575,256 which is incorporated herein by reference.

The float tube assembly 10 of the present invention comprises fixed inner housing 12, floating housing 14 and annular float 16.

The fixed inner housing 12 comprises an elongated annular cylindrical member extending through pump assembly housing 4 and secured to a portion of the pump assembly 3 at the upper end 18 of the fixed inner housing 12. The fixed inner housing 12 contains one or more apertures 20 therein which may be of any desired shape to allow fluid flow therethrough. The length of the fixed inner housing 12 may be any desired length depending upon the size of the digester 1 and the fluids levels therein. Contained on the exterior of inner housing 12 near the lower end thereof is seal 22. The seal 22 may be of any suitable type, such as a scraper-type seal, but need not be a fluid tight seal. The seal 22 need be a sufficient type seal to prevent debris, solids, and liquid from substantially entering the annular space 24 between fixed inner housing 12 and floating housing 14.

The floating housing 14 comprises an elongated annular cylindrical member having one or more apertures 26 through the upper end thereof. The length of the float housing 14 may be any desired length depending upon the size of the digester 1 and the fluid levels therein so long as there is sufficient overlap of the lured inner housing 12 and floating housing 14 to prevent disengagement therebetween. The apertures 26 may be of any suitable size and shape to allow the flow therethrough of liquid, scum and/or foam from the digester 1.

The annular float 16 comprises an elongated annular cylindrical member secured to the upper end of floating housing 14 by any suitable means, such as welding. The annular float 16 contains one or more apertures 28 therein which allow communication with apertures 26 of the floating housing 14. The annular float 16 may be of any suitable length so long as the annular float 16 has sufficient buoyant capacity to float in the anticipated liquid and particulate material in the digester 1 and cause the floatation of the floating housing 14. The annular float 16 may be formed in any suitable manner, such as an annular chamber filled with closed cell foamed material, employing a ballast chamber, employing separate ballast chambers, pontoons, etc.

Attached to the exterior of fixed inner housing 12 are a plurality of elongated arcuate plates 30. Secured to the upper end of floating housing 14 and/or annular float 16 are a plurality of arms 32 or guides having rub blocks 34 secured thereto to rub on plates 30 to guide floating housing 14 with respect to fixed inner housing 12.

As shown in drawing FIG. 1, the floating housing 14 having annular float 16 secured thereto is in its upper most position with respect to the fixed housing 12.

Figure 2:
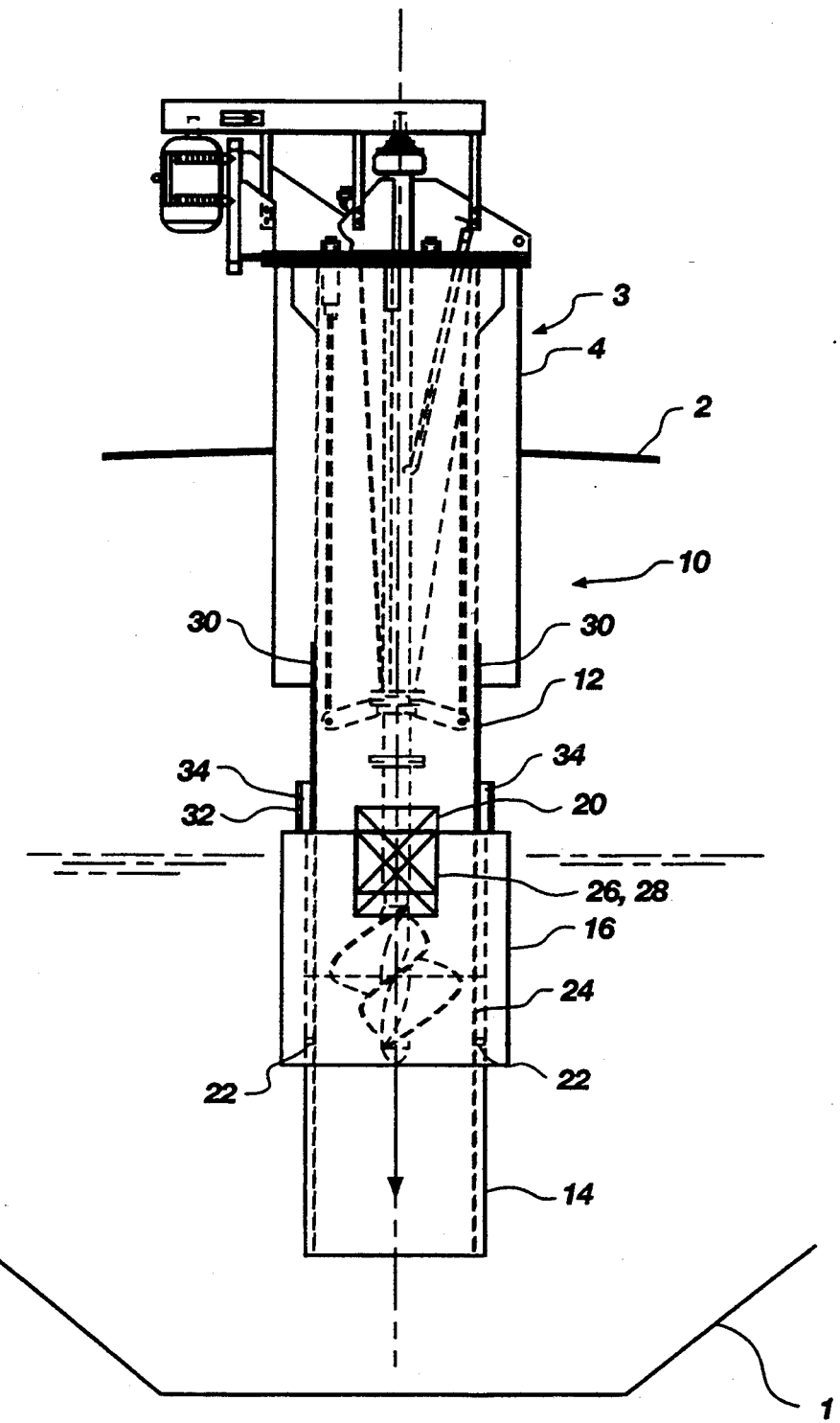
FIG. 2 is a side view of the embodiment of the present invention of FIG. 1 in a digester at its lower liquid level.

Referring to drawing FIG. 2, the floating housing 14 having float 16 secured thereto is shown in its lowest position with respect to the fixed housing 12. In this position, the apertures 26, 28 in float housing 14 and annular float 16 respectively are in close fluid communication. The annular seal 22 maintains the substantial sealing of the annular space 24 between fixed housing 12 and float housing 14.

Figures 3, 4:
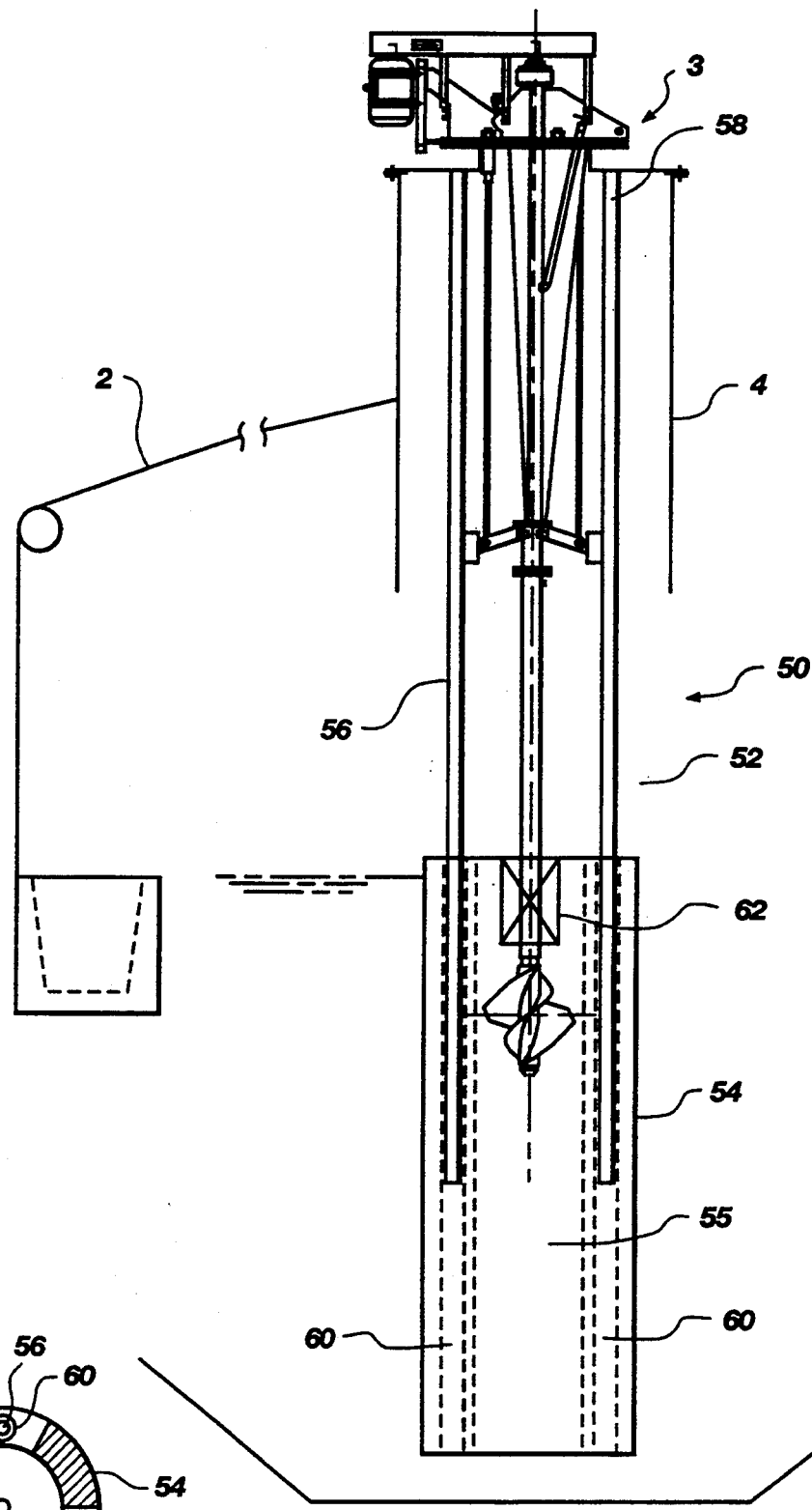
FIG. 3 is a side view of a second embodiment of the present invention in a digester at its lower liquid level.
FIG. 4 is a top view of the second embodiment of the present invention shown in FIG. 3.

Referring to drawing FIG. 3, a second embodiment 50 of the float tube assembly of the present invention is shown.

The float tube assembly 50 comprises float tube guide assembly 52 and floating housing 54.

The float tube guide assembly 52 comprises a plurality of individual guide tube 56 which are typically elongated cylindrical tubes having their upper ends 58 secured to a portion of the mixing apparatus 3. Each guide tube 56 may be any suitable length depending upon the size of the digester 1. The diameter of each tube 56 may be of any convenient size depending on the size of the floating housing 54, the annular wall thickness of floating housing 54 and the desired rigidity of the structure. The lower ends of each guide tube 56 may be sealed, if desired.

The floating housing 54 comprises an elongated annular cylindrical housing having a bore 55 therethrough, a plurality of longitudinal apertures 60 and one or more notches 62 formed in the upper end thereof. If desired, the lower end of each aperture 60 may be sealed. The interior of the floating housing 54 may be filled with any desirable floatation means, such as closed cell foam and other means discussed hereinbefore to provide the necessary floatation of the floating housing 54 within digester 1. As shown, the floating housing 54 is in its lower most position with respect to the digester 1 and mixing apparatus 3 therein.

Referring to drawing FIG. 4, the guide tubes 56 and floating housing 54 are shown from the top. As illustrated, each guide tube 56 is received in longitudinal aperture 60 in the floating housing 54 thereby allowing the floating housing 54 to move longitudinally with respect to the guide tubes 56.

Figure 5:
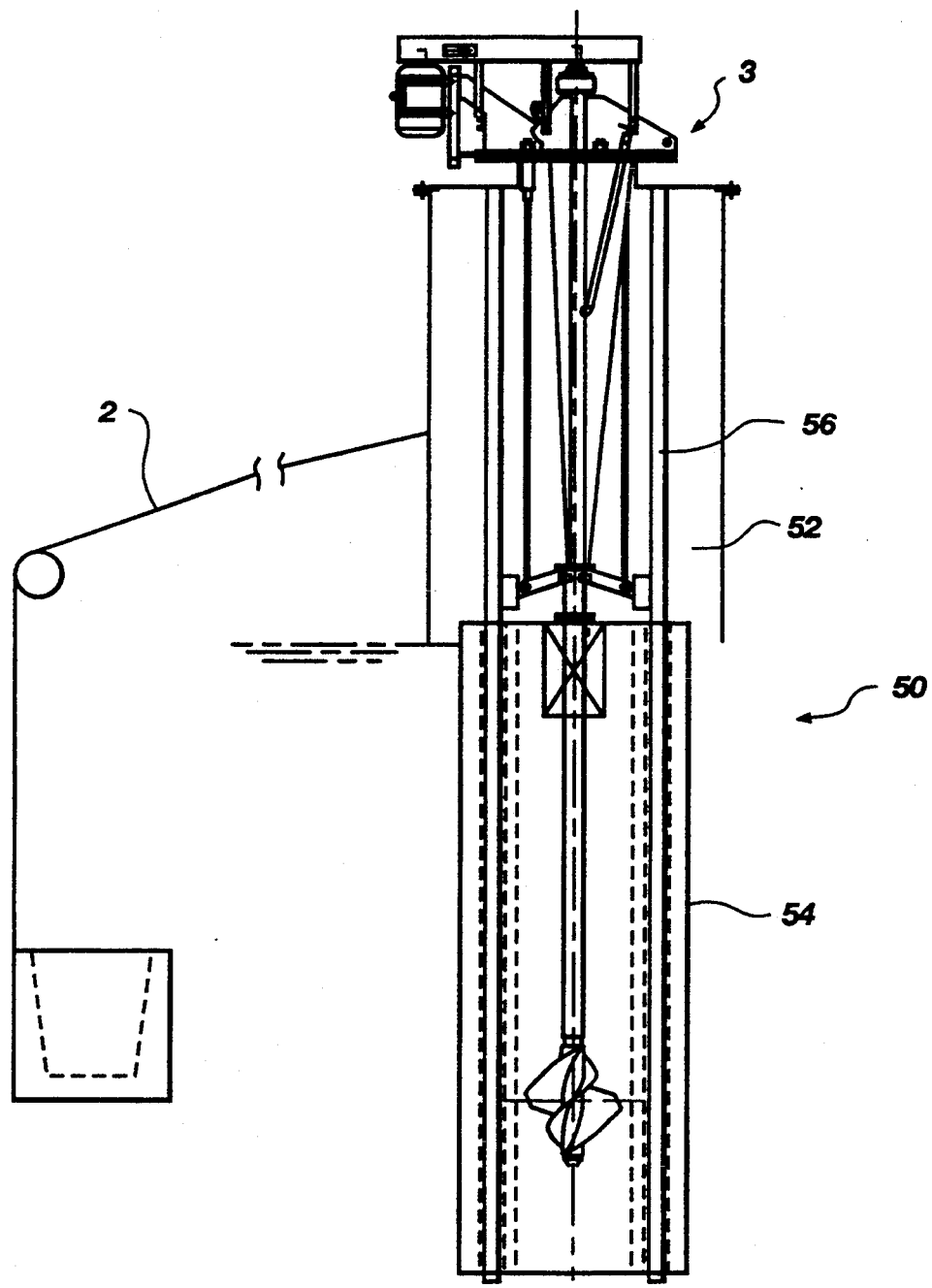
FIG. 5 is a side view of the second embodiment of the present invention shown in FIG. 3 in a digester at its upper liquid level.
Figure 5:

Referring to drawing FIG. 5, the float tube assembly 50 is shown in its upper most position within the digester 1 and mixing apparatus 3 therein.

If desired, the guide tubes 56 may extend beyond the floating housing 54 when it is in its lowest position with each tube 56 having a horizontal flat plate or other means secured on the bottom thereof to prevent the floating housing 54 from disengaging the guide tubes 56.

Figure 6:
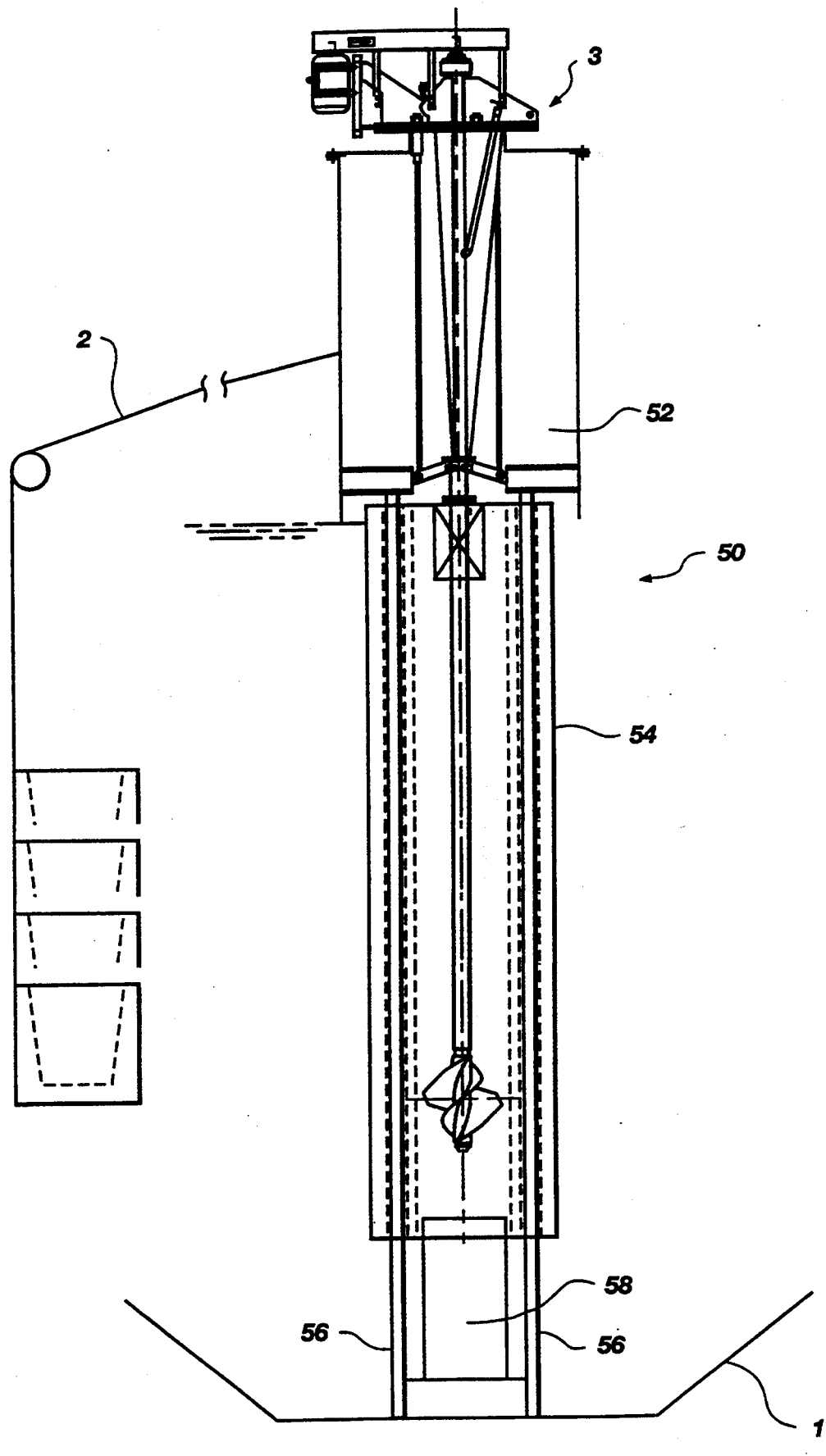
FIG. 6 is a side view of a third embodiment of the present invention in a digester.

Referring to drawing FIG. 6, a third embodiment 50 of the float tube assembly is shown. In the embodiment 50, the guide tubes 56 are secured to the bottom of a digester 1, rather than the mixer. In this manner the floating housing 54 may float with respect to the guide tubes 56. Secured by any suitable means to the lower portions of guide tubes 56 is a fixed housing 58 which serves to direct mixed liquids, scum and foam downwardly into the sludge. The fixed housing 58 has sufficient length to have a portion thereof engaging the bore of float housing 54 when float tube 54 is in its highest position within digester 1. If desired, a seal such as discussed hereinbefore may be included between fixed housing 58 and float housing 54.

Figure 7:
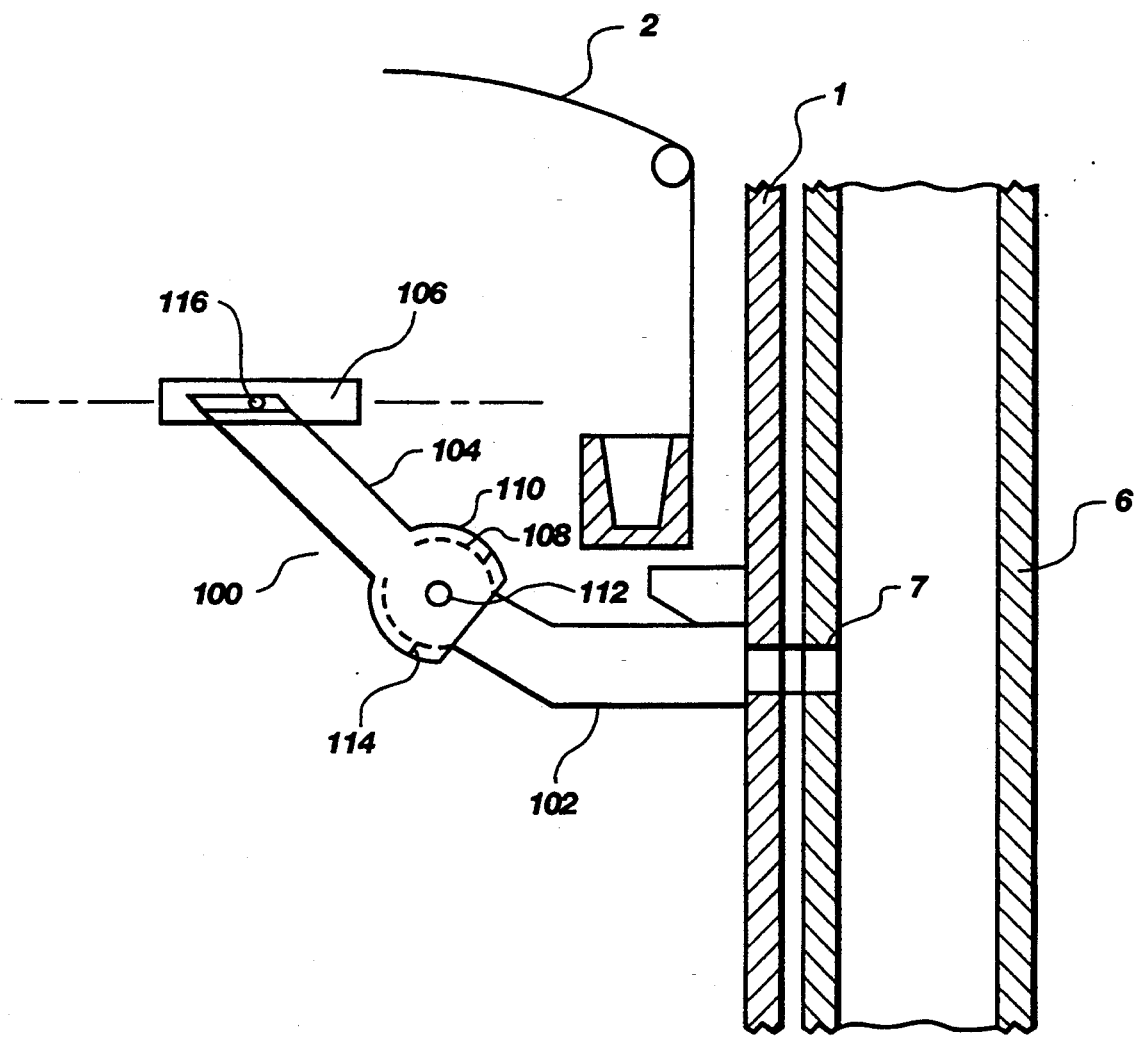
FIG. 7 is a side view of a fourth embodiment of the present invention in a digester having an external mixing chamber.

Referring to drawing FIG. 7, a fourth embodiment 100 of the float tube assembly is shown. The digester 1 has a floating cover 2 thereon. Rather than contain an internal mixing apparatus mounted on or through the cover 2, the digester 1 contains one or more mixing apparatus (not shown) installed in mixing chambers 6 which are located on the exterior of the digester 1. The mixing chambers 6 are in fluid communication with the digester 1 via conduits 7 and float tube assembly 100 connected thereto.

The float tube assembly 100 comprises fixed inner housing 102, floating housing 104 and float 106.

The fixed inner housing 102 comprises an elongated annular cylindrical member having one end thereof in fluid communication with conduit 7 and, the other end thereof, having the male member 108 of a barrel receptacle connection formed thereon. The shape of the male member of the barrel receptacle may be of any desired profile, such as rectangular. The length of the fixed inner housing 102 may be as desired depending upon the size of the digester 1 and the fluids therein.

The floating housing 104 comprises an elongated annular cylindrical member having, on one end thereof, the female portion 110 of a barrel type receptacle and, the other end thereof, being open. The female portion 110 of the barrel mates with male portion 108 of fixed housing 102. The female portion 110 is free to rotate with respect to male portion 108 via cylindrical tube 112 extending therethrough. A seal 114 may be included between fixed housing 102 and floating housing 104, if desired, to keep debris from becoming lodged therebetween in the male portion 108 and female portion 110. The seal 114 may be of any suitable type as discussed hereinbefore to scrape debris from the housing 102, 104 but need not be fluid tight.

The float 106 may be of any suitable type, such as rectangular pontoons filled with closed cell foam or other means discussed hereinbefore, one on each side of the end of the floating housing 104. The float 106 is movably connected to the end of the floating housing 104 via cylindrical tube 116 extending therethrough. In that manner, the end of the floating housing 104 may rise and fall with respect to fixed housing 102 via female portion 110 and male portion 108, respectively, as the fluids levels within the digester 1 rise and fall.

Alternatively, the floating housing 104 may be a large flexible hose or pipe connected to the fixed housing 102 by a suitable flexible bellows or the like, if desired, thereby eliminating the necessity of fabricating a barrel type receptacle.

It will be obvious to those of ordinary skill in the art that additions, deletions, changes and modifications to the present invention can be made which will fall within the scope of the present invention.

Although the float tube assemblies of the present invention has been described with respect to a digester, the float tube assemblies could be used with a mixer in any type biological reactor apparatus where mixing is needed.

It can be easily seen that the float tube assemblies of the present invention offers the advantage that the mixing apparatus may be supplied with liquids from the digester or biological reactor throughout a greater range of operating fluid liquids levels.

What is claimed is:

1. A float tube assembly in combination with a mixing apparatus in a digester having liquids therein during waste disposal processes, said float tube assembly comprising:
    an annular fixed housing having a portion thereof communicating with a portion of said mixing apparatus to allow said liquids in said digester to flow to said mixing apparatus;
    an annular floating housing having a portion thereof installed around the annular fixed housing, the annular floating housing in communication with said liquids in said digester; and
    float means connected to the annular floating housing providing buoyant force to allow the annular floating housing to float in said liquids in said digester while allowing said liquids to flow through the annular floating housing into the annular fixed housing to said mixing apparatus.

2. The float tube assembly of claim 1, wherein the annular fixed housing has an aperture therethrough to allow said liquids in said digester to flow to said mixing apparatus.

3. The float tube assembly of claim 2, wherein said annular floating housing has an aperture therein to allow said liquids in said digester to flow to annular fixed housing.

4. The float tube assembly of claim 1, wherein the annular floating housing has an aperture therein to allow said liquids in said digester to flow to the annular fixed housing.

5. The float tube assembly of claim 1, wherein the float means comprise an annular float means connected to the annular floating housing.

6. The float tube assembly of claim 1, wherein the float means comprise a pontoon float means connected to the annular floating housing.

7. The float tube assembly of claim 1, wherein the annular floating housing is movably connected to the annular fixed housing to allow for the variation in the level of said liquids in said digester.

8. The float tube assembly of claim 1, wherein the annular floating housing is pivotally connected to the annular fixed housing to allow for the variation in the level of said liquids in said digester.

9. The float tube assembly of claim 1 further comprising:
    seal means located between the annular fixed housing and the annular floating housing to prevent debris in said liquids in said digester entering into the area between the annular fixed housing and the annular floating housing.

10. In combination, a float tube assembly and a mixing apparatus installed in the floating cover of a digester having liquids therein during waste disposal processes, said mixing apparatus having a portion thereof extending into said liquids into said digester to mix said liquids during waste disposal processes, said float tube assembly comprising:
    an annular fixed housing connected to a portion of said mixing apparatus and installed around said portion of said mixing apparatus extending into said liquids in said digester, the annular fixed housing having an aperture therein to allow said liquids to communicate with said portion of said mixing apparatus;
    an annular floating housing having a portion thereof installed around the annular fixed housing, the annular floating housing in communication with said liquids in said digester, the annular floating housing having means to allow the flow of said liquids to the annular fixed housing; and
    float means connected to the annular floating housing providing buoyant force to allow the annular floating housing to float in said liquids in said digester while allowing said liquids to flow through the annular floating housing into the annular fixed housing to said mixing apparatus.

11. A float tube assembly in combination with a mixing apparatus in a biological reactor having liquids therein during biological processes, said float tube assembly comprising:
    an annular fixed housing having a portion thereof communicating with a portion of said mixing apparatus to allow said liquids in said reactor to flow to said mixing apparatus;
    an annular floating housing having a portion thereof installed around the annular fixed housing, the annular floating housing in communication with said liquids in said reactor; and
    float means connected to the annular floating housing providing buoyant force to allow the annular floating housing to float in said liquids in said reactor while allowing said liquids to flow through the annular floating housing into the annular fixed housing to said mixing apparatus.

12. The float tube assembly of claim 11, wherein the annular fixed housing has an aperture therethrough to allow said liquids in said reactor to flow to said mixing apparatus.

13. The float tube assembly of claim 12, wherein said annular floating housing has an aperture therein to allow said liquids in said reactor to flow to annular fixed housing.

14. The float tube assembly of claim 11, wherein the annular floating housing has an aperture therein to allow said liquids in said reactor to flow to the annular fixed housing.

15. The float tube assembly of claim 11, wherein the float means comprise an annular float means connected to the annular floating housing.

16. The float tube assembly of claim 11, wherein the float means comprise a pontoon float means connected to the annular floating housing.

17. The float tube assembly of claim 11, wherein the annular floating housing is movably connected to the annular fixed housing to allow for the variation in the level of said liquids in said reactor.

18. The float tube assembly of claim 11, wherein the annular floating housing is pivotally connected to the annular fixed housing to allow for the variation in the level of said liquids in said reactor.

19. The float tube assembly of claim 11 further comprising:

seal means located between the annular fixed housing and the annular floating housing to prevent debris in said liquids in said digester entering into the area between the annular fixed housing and the annular floating housing.

20. The float tube assembly of claim 11 further comprising:

guide means secured to the floating housing to guide the floating housing with respect to the fixed housing.

21. The float tube assembly of claim 11 further comprising guide means secured to the floating housing and the float means to guide the floating housing with respect to the fixed housing.

22. In combination, a float tube assembly and a mixing apparatus installed in the floating cover of a biological reactor having liquids therein during biological processes, said mixing apparatus having a portion thereof extending into said liquids into said reactor to mix said liquids during biological processes, said float tube assembly comprising:

an annular fixed housing connected to a portion of said mixing apparatus and installed around said portion of said mixing apparatus extending into said liquids in said reactor, the annular fixed housing having an aperture therein to allow said liquids to communicate with said portion of said mixing apparatus;

an annular floating housing having a portion thereof installed around the annular fixed housing, the annular floating housing in communication with said liquids in said reactor, the annular floating housing having means to allow the flow of said liquids to the annular fixed housing; and float means connected to the annular floating housing providing buoyant force to allow the annular floating housing to float in said liquids in said reactor while allowing said liquids to flow through the annular floating housing into the annular fixed housing to said mixing apparatus.

* * * * *